(12) United States Patent
Yunoki et al.

(10) Patent No.: US 7,220,698 B2
(45) Date of Patent: May 22, 2007

(54) CATALYST FOR CATALYTIC GAS PHASE OXIDATION OF ACROLEIN AND PROCESS FOR PRODUCING ACRYLIC ACID BY CATALYTIC GAS PHASE OXIDATION USING SAID CATALYST

(75) Inventors: Hiromi Yunoki, Himeji (JP); Michio Tanimoto, Himeji (JP)

(73) Assignee: Nippon Shokubai Co., Ltd., Osaka (JP)

( * ) Notice: Subject to any disclaimer, the term of this patent is extended or adjusted under 35 U.S.C. 154(b) by 302 days.

(21) Appl. No.: 11/052,897

(22) Filed: Feb. 9, 2005

(65) Prior Publication Data

US 2005/0176995 A1 Aug. 11, 2005

(30) Foreign Application Priority Data

Feb. 10, 2004 (JP) ............................. 2004-033647

(51) Int. Cl.
*B01J 23/00* (2006.01)
*C01C 51/235* (2006.01)
(52) U.S. Cl. ...................................... 502/312; 562/535
(58) Field of Classification Search ............... None
See application file for complete search history.

(56) References Cited

U.S. PATENT DOCUMENTS 5,719,318 A 2/1998 Kawajiri et al.

6,563,000 B1 5/2003 Yunoki et al.

FOREIGN PATENT DOCUMENTS

| EP | 0 792 866 | 9/1997 |
|---|---|---|
| EP | 1 055 662 | 11/2000 |
| JP | 53-30688 | 8/1978 |
| JP | 7-10802 | 1/1995 |
| JP | 9-241209 | 9/1997 |
| JP | 2000-336060 | 12/2000 |

*Primary Examiner*—Paul A. Zucker
(74) *Attorney, Agent, or Firm*—Wenderoth, Lind & Ponack, L.L.P.

(57) ABSTRACT

There are provided a catalyst for catalytic gas phase oxidation of acrolein with molecular oxygen to produce acrylic acid, the catalyst including molybdenum and vanadium and further including at least one volatile catalyst poison ingredient in an amount of 10 to 100 ppb by mass as measured by ion chromatography; and a process for producing acrylic acid, including a step of carrying out catalytic gas phase oxidation of acrolein with molecular oxygen using the catalyst. The catalyst of the present invention can lower a hot spot temperature and suppress reduction in a reaction efficacy accompanied with thermal degradation, so that the acrolein conversion can stably be kept higher over a long term.

11 Claims, No Drawings

CATALYST FOR CATALYTIC GAS PHASE OXIDATION OF ACROLEIN AND PROCESS FOR PRODUCING ACRYLIC ACID BY CATALYTIC GAS PHASE OXIDATION USING SAID CATALYST

FIELD OF THE INVENTION

The present invention relates to a catalyst which is suitable for producing acrylic acid, and a process for producing acrylic acid using the catalyst. More specifically, the present invention relates to a catalyst used when acrylic acid is produced in such a manner that acrolein is subjected to catalytic gas phase oxidization with molecular oxygen, as well as a process of catalytic gas phase oxidation using the catalyst.

BACKGROUND OF THE INVENTION

As a catalyst used when acrylic acid is produced in such a manner that acrolein is subjected to catalytic gas phase oxidation with molecular oxygen, there has widely been used a catalyst containing molybdenum and vanadium as essential components (hereinafter referred to as the molybdenum-vanadium catalyst in some cases) The molybdenum-vanadium catalyst has been known to have higher activity (in which an acrolein conversion may sometimes be used in place of activity) as compared with other catalysts. In usual cases, when catalytic gas phase oxidation of acrolein is carried out using a fixed-bed catalytic reactor filled with a catalyst, since the oxidation is accompanied with heat generation, a "hot spot" (i.e., a local abnormally high temperature part) is generated in the catalyst bed. When this hot spot has a too high temperature, the occurrence of excessive oxidation allows thermal degradation of the catalyst to proceed and further induces run away reaction.

As one means of solving the above problem, various techniques have been proposed in which a catalyst bed is divided into some parts in a tube axial direction of the catalyst reactor, the activity of a catalyst to be filled in the reaction gas inlet side on which a hot spot may easily be formed being set lower than that of a catalyst to be filled in the reaction gas outlet side.

For example, there have been proposed techniques in which a catalyst having activity lowered by incorporation of an inert substance is filled in the reaction gas inlet side of a catalyst bed (e.g., JP-B 53-30688 (1978)) and techniques in which the ratio of an active component carried on a carrier to be filled in the reaction gas inlet side is lowered (e.g., JP-A 07-10802 (1995)). In addition, there have also been proposed techniques in which a catalyst having activity lowered by addition of, for example, an alkali metal is filled (e.g., JP-A 2000-336060) and techniques in which the particle diameter of a catalyst to be filled in the reaction gas inlet side is set larger than that of a catalyst to be filled in the reaction gas outlet side (e.g., JP-A 09-241209 (1997)).

In usual cases, catalytic activity is gradually lowered by thermal degradation and the like, so that the acrolein conversion is reduced when operation time (i.e., duration of oxidation) becomes longer. Therefore, in order to keep the acrolein conversion higher, it is necessary to raise the reaction temperature. However, when the reaction temperature is raised, thermal degradation of a catalyst further proceeds. Therefore, when a catalyst having lower activity is filled in the reaction gas inlet side of a catalyst bed as in the above prior art, some effect is attained for the control of a hot spot temperature, but it cannot be said that this has sufficient productivity for a long term because of a lowering of activity. As a matter of course, productivity may be increased by setting the reaction temperature higher even in the prior art. However, since some problems arise on the thermal degradation of a catalyst and the formation of a hot spot, this is also not practical.

SUMMARY OF THE INVENTION

The present invention has been made in view of the above problems, and it is an object of the present invention to provide a catalyst which lowers the hot spot temperature, suppresses a lowering in the activity of a catalyst by thermal degradation, and can stably keep the acrolein conversion higher for a long term; and a process of catalytic gas phase oxidation using the catalyst.

Thus the present invention provides a catalyst for catalytic gas phase oxidation of acrolein with molecular oxygen to produce acrylic acid, the catalyst comprising molybdenum and vanadium and further comprising at least one volatile catalyst poison ingredient in an amount of 10 to 100 ppb by mass as measured by ion chromatography.

The above volatile catalyst poison ingredient is preferably detected as an inorganic ion by ion chromatography. The inorganic ion is more preferably an ammonium ion.

The present invention further provides a process for producing acrylic acid, comprising a step of carrying out catalytic gas phase oxidation of acrolein with molecular oxygen using at least one catalyst, wherein the catalyst comprises molybdenum and vanadium and further comprises at least one volatile catalyst poison ingredient in an amount of 10 to 100 ppb by mass as measured by ion chromatography.

The above catalytic gas phase oxidation of acrolein with molecular oxygen is preferably carried out with a fixed-bed shell-and-tube catalytic reactor with at least one catalyst bed containing the above catalyst.

The content of the above volatile catalyst poison ingredient in the catalyst is more preferably set substantially constant over the catalyst bed.

Alternatively, the catalyst bed is more preferably divided into two or more parts in a tube axial direction of the catalytic reactor and wherein a content of the volatile catalyst poison ingredient in the catalyst is set lower in one part of the catalyst bed positioned on a reaction gas outlet side of the catalyst bed than in another part, adjacent to said one part, of the catalyst bed positioned on a reaction gas inlet side of the catalyst bed.

Alternatively, the catalyst bed is more preferably divided into three or more parts in a tube axial direction of the catalytic reactor and wherein a content of the volatile catalyst poison ingredient in the catalyst is set lower in one part of the catalyst bed positioned on a reaction gas outlet side of the catalyst bed than in another part of the catalyst bed positioned on a reaction gas inlet side of the catalyst bed and wherein the content of the volatile catalyst poison ingredient in the catalyst shows a rise and then lowering in an intermediate part of the catalyst bed positioned between the reaction gas inlet side and the reaction gas outlet side of the catalyst bed.

The above acrolein is preferably obtained by preceding oxidation in which propylene is subjected to catalytic gas phase oxidation with molecular oxygen in the presence of a catalyst comprising molybdenum, bismuth, and iron.

The above volatile catalyst poison ingredient is preferably detected as an inorganic ion by ion chromatography. The inorganic ion is more preferably an ammonium ion.

As described above, in the present invention, by allowing a specific amount of volatile catalyst poison ingredient to be contained in a catalyst originally having high activity, catalytic activity is transiently decreased, so that a hot spot temperature can be lowered. At the same time, by gradually loosing the volatile catalyst poison ingredient by reaction heat, catalytic activity is recovered, so that a lowering of activity by thermal degradation of the catalyst can be suppressed. Thus, the acrolein conversion can stably be kept higher for a long term.

DETAILED DESCRIPTION OF THE INVENTION

The present inventors have found the following fact. When the catalytic gas phase oxidation of acrolein with molecular oxygen is carried out using a fixed-bed shell-and-tube catalytic reactor filled with at least one molybdenum-vanadium catalyst, the temperature of a hot spot at the early stage after the reaction initiation becomes highest; however, the temperature of the hot spot is then gradually lowered and will soon become stable at a substantially constant temperature.

Thus, the present inventors have thought that, if the hot spot temperature at the early stage is suppressed, even when the reactor is operated for a long term thereafter, the above problems, such as run away reaction resulting from the hot spot, do not arise. They have studied a method of suppressing the hot spot temperature at the early stage and also have intensively studied a method of suppressing a lowering of the activity of a catalyst by thermal degradation and keeping the acrolein conversion higher when the reactor is worked for a further long term.

As a result, they have found that, when a specific amount of at least one volatile catalyst poison ingredient is contained in a molybdenum-vanadium catalyst, the hot spot temperature can be lowered, and a problem of a reduction in acrolein conversion occurring with long-term working can also be solved.

The catalyst of the present invention comprises two essential elements, i.e., molybdenum and vanadium, as catalyst active components which contribute to the reaction, and it further comprises at least one volatile catalyst poison ingredient which is lost by reaction heat or the like.

When a volatile catalyst poison ingredient is contained, catalyst active sites are poisoned, leading to an activity-deficient condition, so that the acrolein conversion is lowered and the amount of reaction heat is reduced; therefore, the hot spot temperature at the early stage, which has been problematic, can be suppressed. Moreover, the volatile catalyst poison ingredient is gradually volatilized and lost with time by reaction heat or the like, so that activity becomes recovered therewith. Therefore, when the reactor is operated for a long term, the acrolein conversion can be kept higher. In other words, the catalyst gradually causes thermal degradation by reaction heat, but the activity of the catalyst is recovered as the volatile catalyst poison ingredient becomes lost; therefore, a reduction in acrolein conversion can be suppressed. For this reason, a rise of reaction temperature needed to keep the acrolein conversion can be suppressed lower than a conventional one; the degree of progression of thermal degradation by a rise of reaction temperature can also be suppressed; and the life of the catalyst can be prolonged.

In order to enhance the above hot spot temperature suppressing effect attained by a volatile catalyst poison ingredient, it is desirable to increase the content of the volatile catalyst poison ingredient. However, when the content is too much increased, catalytic activity is considerably lowered to make insufficient the acrolein conversion at the early stage of working, leading to a reduction in productivity. In addition, a volatile catalyst poison ingredient adsorbed onto the active site of the catalyst is not sufficiently lost and remains even when oxidation is continued for a long term, so that the activity of a catalyst is not necessarily recovered.

Therefore, it is desirable that the content of the volatile catalyst poison ingredient is preferably 100 ppb by mass or lower, more preferably 80 ppb by mass or lower, and still more preferably 70 ppb by mass or lower. On the other hand, when the content of the volatile catalyst poison ingredient is too low, the hot spot temperature cannot sufficiently be lowered. Therefore, it is desirable that the content of the volatile catalyst poison ingredient is preferably 10 ppb by mass or higher, more preferably 20 ppb by mass or higher, and sill more preferably 25 ppb by mass or higher. When two or more volatile catalyst poison ingredients are used, the above contents are in total. The determination of the content of the volatile catalyst poison ingredient may be determined taking into consideration, for example, factors influencing on activity, such as catalyst composition, catalyst size, and supported rate (in the case of a supported catalyst).

In the present invention, the volatile catalyst poison ingredient is measured by the following method.

First, 3 g of catalyst components (in the case of a supported catalyst, catalyst components removed from a carrier) is weighed precisely, and put into a clean glass vessel. The vessel is placed in a tubular furnace with a gas flowmeter. Then, three gas washing bottles (each of which has a volume of 25 $cm^3$ and has been allowed to contain 15 $cm^3$ of ion-exchanged water and then cooled to about 1° C. with ice water) are connected in series to the gas outlet side of the tubular furnace. While helium gas is allowed to pass at a rate of 100 $cm^3$/min through the tubular furnace, the catalyst component is heated to 500° C. for 60 minutes, and the total volume of a gas desorbed from the catalyst is introduced and collected into the gas washing bottles. After heating for 60 minutes, the temperature of the catalyst component is returned to room temperature, all the liquids in the gas washing bottles is placed into a volumetric flask, ion-exchanged water is further added to the flask to a total liquid amount of 100 $cm^3$, and a volatile catalyst poison ingredient in the catalyst component is measured with an ion chromatographic apparatus using the liquid in the measuring flask as a sample solution, to calculate the content of the volatile catalyst poison ingredient per unit mass of the catalyst component.

In the present invention, for collecting the volatile catalyst poison ingredient in the catalyst component is used PROGRAMMABLE FURNACE QF-02 (manufactured by Mitsubishi Kasei K.K.) and as the ion chromatographic test apparatus is used DX-320 (manufactured by DIONEX) The measuring conditions for ion chromatography are as follows: column, CS12A (for cations) ; oven and detector temperature, 35° C., and sample solution injection rate, $5 \times 10^{-8}$ $m^3$.

For example, when ammonia is used as a raw material of the volatile catalyst poison ingredient, the content of the volatile catalyst poison ingredient can be determined by measuring the amount of an ammonium ion with an ion chromatographic apparatus.

In the present invention, the volatile catalyst poison ingredient refers to an ingredient having the property of reducing catalytic activity and the property of being lost (referred to as desorption in some cases) from the catalyst by gradual volatilization during the oxidization.

The gradual volatilization refers to not loss of the entire amount of a volatile catalyst poison ingredient from the catalyst, but loss of the catalyst poison ingredient little by little with time, at a time when the temperature reaches a specific temperature (volatilization temperature). In the meantime, since the amount of loss and the time needed for loss depend upon reaction conditions such as reaction temperature and catalyst physical properties such as catalyst poison content and catalyst composition (by which adsorptivity to the catalyst poison ingredient is changed), they may appropriately be adjusted so that the volatile catalyst poison ingredient is lost when a desired time has passed. Therefore, although the amount of the remaining volatile catalyst poison ingredient contained in the catalyst is decreased with time, the volatile catalyst poison ingredient may or may not at all remain in the catalyst depending upon use conditions and the like.

As the catalyst poison ingredient, preferable is neither a nonvolatile catalyst poison ingredient nor a catalyst poison ingredient hardly volatile under ordinary reaction conditions for producing acrylic acid. Therefore, in the present invention, it is necessary to use a volatile catalyst poison ingredient having the property of being lost under reaction conditions employed in the ordinary step of producing acrylic acid.

The volatile catalyst poison ingredient used in the present invention may be either organic or inorganic. In the present invention, two or more volatile catalyst poison ingredients may be used in combination. Examples of the raw material of an organic volatile catalyst poison ingredient include amines and pyridines. Examples of the raw material of an inorganic volatile catalyst poison ingredient include nitrogen compounds. In the present invention, an inorganic volatile catalyst poison ingredient is preferable; an inorganic ion which can be measured by ion chromatography is more preferable; and an ammonium ion is still more preferable. These ingredients have an appropriate rate of loss with time under ordinary reaction conditions for producing acrylic acid, and they are effective in controlling the hot spot temperature and preventing a lowering of activity by thermal degradation of the catalyst. In particular, when ammonia is used as a raw material and contained in the above specific amount as the catalyst poison ingredient of a molybdenum-vanadium catalyst, there can be attained a better balance between adsorption and desorption, and this is effective in not only controlling the hot spot temperature, but also preventing a lowering of activity by thermal degradation, so that the acrolein conversion can be kept higher.

When the volatile catalyst poison ingredient is contained in the molybdenum-vanadium catalyst using a raw material such as ammonia, the catalyst poison ingredient is only adsorbed onto the active site of the catalyst; therefore, it is gradually volatilized from the catalyst by exposure to oxidation reaction heat, and the activity of the catalyst at the poisoned part is recovered (i.e., it contributes to the reaction). In addition, the amount of the volatile catalyst poison ingredient contained in the catalyst is small, and the ingredient is gradually volatilized from the catalyst over a long time, so that the ingredient has no influence on the process of purifying acrylic acid after the oxidation. The volatile catalyst poison ingredient introduced using ammonia as a raw material into the catalyst is not adsorbed after the volatilization onto a catalyst arranged downstream, which is therefore preferable.

As the catalyst to be allowed to contain the above volatile catalyst poison ingredient, there may be used a catalyst which can promote the catalytic gas phase oxidation of acrolein (including acrolein-containing gases; the same in the following) with molecular oxygen (including molecular oxygen-containing gases; the same in the following), with particularly desirable being a molybdenum-vanadium catalyst. For example, a catalyst containing an oxide and/or a composite oxide in a specific range, which is represented by the following general formula (1), allows the production of acrylic acid in high yield for a long term, which is therefore preferable.

$$Mo_aV_bW_cCu_dO_x \qquad (1)$$

wherein Mo, V, W, Cu, and O are molybdenum, vanadium, tungsten, copper, and oxygen elements; a, b, c, d, and x are the atomic ratios of Mo, V, W, Cu, and O, respectively; when a=12, then $1 \leq b \leq 14$, $0 < c \leq 12$, and $0 < d \leq 10$; and x is a numerical value determined by the oxidation states of the Mo, V, W, and Cu elements.

In the present invention, any metal element may be contained in addition to the Mo, V, W, and Cu elements represented in the general formula (1). Examples of such a metal element include niobium, chromium, manganese, iron, cobalt, nickel, zinc, bismuth, tin, and antimony.

A process for producing the catalyst of the present invention will hereinafter be described; however, the process may appropriately be altered or modified, or any process other than the following process may be employed.

The process for producing a molybdenum-vanadium catalyst is not particularly limited, and this catalyst can be produced by any of the conventional processes. The catalyst represented by the above general formula (1) can also be produced by any of the known catalyst preparing processes. For example, when the catalyst represented by the above general formula (1) is produced, a starting raw material is not particularly limited, but there may be used various metal compounds which are generally used, such as ammonium salts, nitrate salts, carbonate salts, sulfate salts, hydroxides or oxides of a metal, or composite compounds containing two or more metals.

The molybdenum-vanadium catalyst is not limited to a formed catalyst in which a catalyst component containing molybdenum and vanadium is formed into a desired shape, and it may be a supported catalyst in which the catalyst component is supported by any carrier. The kind of carrier is not particularly limited, and the use of an inert carrier is desirable, examples of which include alumina, silica, silica-alumina, silicon carbide, pumice, zirconia, titania, zeolite, magnesia, steatite, and titania-silica. In addition, the shape of the catalyst is not limited, and it may be any of spherical, tubular (or pellet), ring, honeycomb, and amorphous shapes. In these shapes, particularly desirable are catalysts in spherical or tubular (or pellet) shape.

The catalyst size may appropriately be determined depending upon the diameter of a reaction tube in which the catalyst is filled. For example, when the catalyst is in spherical shape, it is desirable that the catalyst preferably has a diameter of 3 mm or greater, more preferably 4 mm or greater and the catalyst preferably has a diameter of 15 mm or smaller, more preferably 10 mm or smaller.

A process for producing a formed catalyst is not particularly limited, and any of the known processes such as extrusion and tablet may be employed. The formed catalyst can be obtained, for example, by adding to water, a molybdenum compound (e.g., molybdic acid, molybdenum trioxide), a vanadium compound (e.g., vanadium pentoxide, a vanadate salt), preferably a tungsten compound (e.g., tungsten trioxide, a tungstate salt) and a copper compound (e.g., copper chloride, copper nitrate, copper oxide), and further a compound containing any metal element such as niobium; heating a slurry obtained by mixing it to evaporate water; drying to solidify it, followed by grinding; if necessary, allowing the ground material to contain a forming aid and a binder; extruding it by extrusion into a desired size and, if necessary, forming it into a desired shape; and firing it at a temperature, which is preferably 300° C. or higher, more preferably 380° C. or higher, and which is preferably 450° C. or lower, more preferably 420° C. or lower, for 1 to 10 hours.

A process for producing a supported catalyst is also not limited, and a catalyst component may be supported by a carrier according to any of the known processes. The supported catalyst can be obtained, for example, by putting a carrier such as silicon carbide, steatite, silica-alumina, or ceria into a slurry containing a desired catalyst component; and evaporating water to dry it at a desired temperature. Alternatively, there can be employed a process of drying a slurry containing a catalyst component; if necessary, grinding it to obtain a powder; putting the powder and a carrier into a rolling granulator for the support of the catalyst component by the carrier using a liquid binder. In the case of a supported catalyst, the supported rate of a catalyst component may appropriately be determined taking into consideration the conditions of oxidation, and the supported rate is preferably 10% by mass or higher, more preferably 15% by mass or higher, and is preferably 70% by mass or lower, more preferably 50% by mass or lower. The supported rate refers to a value calculated by the method described below in Examples.

In the known processes described above, a volatile catalyst poison ingredient may be contained as an impurity in the catalyst; however, such an impurity is usually contained in an extremely small amount lower than the content of the catalyst poison ingredient as defined in the present invention, so that it has no effect such as controlling the hot spot temperature when contained in a specific amount as described above.

Therefore, in order to obtain a catalyst containing a volatile catalyst poison ingredient in a specific amount, it is necessary to add the volatile catalyst poison ingredient to the catalyst, for example, by adding the volatile catalyst poison ingredient during the catalyst preparing process to adjust the content thereof, or by covering the produced catalyst with the volatile catalyst poison ingredient to adjust to a desired content thereof.

Examples of the method of adding a volatile catalyst poison ingredient to a catalyst include:

I. a method of adding a volatile catalyst poison ingredient in the step of preparing a slurry containing a catalyst component; and II. a method of adding a forming aid or a binder, containing a volatile catalyst poison ingredient, in the step of forming a powder containing a catalyst component into a desired shape or in the step of making the catalyst component supported by a carrier.

The content of a volatile catalyst poison ingredient may be adjusted by increasing or decreasing the amount of the volatile catalyst poison ingredient to be added in the above producing step. Examples of the method of adjusting the content of a volatile catalyst poison ingredient added to a catalyst as described above include a method of firing the catalyst while a water vapor-containing gas is flown. Even if the firing temperature and the firing time are the same, a greater amount of the catalyst poison ingredient added can be removed when the concentration of water vapor is higher. Therefore, the content of the volatile catalyst poison ingredient can be adjusted by increasing or decreasing the concentration of water vapor in the flowing gas. The concentration of water vapor when the volatile catalyst poison ingredient is decreased is, for example, preferably 10% by volume or higher.

In the present invention, the constitution of a catalyst bed is not particularly limited. The catalyst bed may be filled at least with a molybdenum-vanadium catalyst containing the above specific amount of a volatile catalyst poison ingredient. For example, the catalyst bed may be filled with a molybdenum-vanadium catalyst containing the above specific amount of a volatile catalyst poison ingredient and another molybdenum-vanadium catalyst containing a volatile catalyst poison ingredient in an amount outside the above range.

For example, even when a catalyst having substantially the same content of a volatile catalyst poison ingredient is filled (in this case, the content of a volatile catalyst poison ingredient is substantially the same from the reaction gas inlet side to the reaction gas outlet side), the advantages of the present invention, e.g., the effect of controlling the hot spot temperature and the recovery of activity by the loss of a volatile catalyst poison ingredient with time, can be attained.

However, in order to obtain higher productivity, it is desirable to fill two or more catalysts having different contents of a volatile catalyst poison ingredient in two or more parts obtained by dividing a catalyst bed in the tube axial direction of a catalytic reactor. The number of parts in the catalyst bed when divided is not particularly limited. In general, there is a tendency that when the number of parts in the catalyst bed is greater, it becomes easy to control the hot spot temperature. However, for example, in the production on an industrial scale, the hot spot temperature can sufficiently be controlled when a catalyst bed is divided into two or three parts.

The optimal value of the ratio of parts in a catalyst bed (i.e., the ratio of division of a catalyst bed) when two or more catalysts are filled in the catalyst bed is different depending upon oxidation conditions as well as the composition, shape, and particle diameter of a catalyst to be filled in each part of the catalyst bed. Therefore, the above ratio may be determined so that optimal catalyst performance can be obtained as a whole.

When two or more catalysts are filled in the catalyst bed, a catalyst containing the above specific amount of the volatile catalyst poison ingredient may be filled in at least one of the parts obtained by the division of the catalyst bed. In the other parts of the catalyst bed, there may be used one or more catalysts each having a content of the volatile catalyst poison ingredient outside the above range.

The catalyst filling method for filling two or more catalysts in a catalyst bed is not particularly limited. For example, there is a method of filling two or more catalysts in a catalyst bed so that the content of a volatile catalyst poison ingredient becomes smaller in one part after another part from the reaction gas inlet side towards the reaction gas outlet side of the catalyst bed. In other words, the catalyst bed is divided into two or more parts in the tube axial direction of a fixed-bed shell-and-tube catalytic reactor and two or more catalysts are respectively filled in these two or more parts of the catalyst bed so that the content of a volatile catalyst poison ingredient in the catalysts is set lower in one part of the catalyst bed positioned on the reaction gas outlet side of the catalyst bed than in another part, adjacent to said one part, of the catalyst bed positioned on the reaction gas inlet side of the catalyst bed. In this case, the length of a catalyst to be filled in the part positioned on the reaction gas inlet side of the catalyst bed is preferably 60% or less, more preferably 50% or less, and still more preferably 40% or less, based on the total length of the catalyst bed. By filling two or more catalysts having different volatile catalyst poison ingredient contents in a catalyst bed in such a manner, heat accumulation at a hot spot can be prevented, and the acrolein conversion can stably be kept higher for a long term.

As another catalyst filling method, there is a method of filling three or more catalysts in a catalyst bed so that the content of a volatile catalyst poison ingredient is increased once and then decreased from the reaction gas inlet side towards the reaction gas outlet side of the catalyst bed. In other words, the catalyst bed is divided into three or more parts in the tube axial direction of a fixed-bed shell-and-tube catalytic reactor and the content of a volatile catalyst poison ingredient in the catalysts is set lower in one part of the catalyst bed positioned on the reaction gas outlet side of the catalyst bed than in another part of the catalyst bed positioned on the reaction gas inlet side of the catalyst bed and the content of the volatile catalyst poison ingredient in the catalyst shows a rise and then lowering in an intermediate part of the catalyst bed positioned between the reaction gas inlet side and the reaction gas outlet side of the catalyst bed. For example, when a catalyst bed is divided into three parts, the content of a volatile catalyst poison ingredient in the catalyst filled in the central part is the highest. When a catalyst bed is divided into three or more parts, the length of a catalyst to be filled in the part positioned on the gas inlet side of the catalyst bed is preferably 50% or less, more preferably 30% or less, and still more preferably 20% or less, based on the total length of the catalyst bed.

In the present invention, when two or more catalysts are filled in a catalyst bed, the language "two or more" means that, using the content of a volatile catalyst poison ingredient as a criterion, if two or more catalysts have substantially the same content of a volatile catalyst poison ingredient, these catalysts are regarded as the same catalysts, even if the compositions and particle diameters of these catalysts are different from one another. Further, in the case of supported catalysts, similarly, the content of a volatile catalyst poison ingredient is used as a criterion, and the supported rate of these catalysts may be different from one another. In addition, in the present invention, a catalyst to be filled in each part of a catalyst bed may be either a formed catalyst or a supported catalyst, or alternatively, these catalysts may be used in any combination. For example, one or more formed catalysts may be filled in the reaction gas inlet side of a catalyst bed and one or more supported catalysts may be filled in the reaction gas outlet side of the catalyst bed.

Thus, the present invention may appropriately be combined with the conventional known hot spot controlling methods, for example, a technique of mixing an inert substance in a catalyst to be filled in the reaction gas inlet side of a catalyst bed to reduce the catalytic activity, a technique of lowering the supported rate of a catalyst to be filled in the reaction gas inlet side of a catalyst bed, a technique of changing the kind and/or amount of an alkali metal to be added to catalysts to make the activity of the catalyst to be filled in the reaction gas inlet side of a catalyst bed lower than that of the catalyst to be filled in the reaction gas outlet side of the catalyst bed, or a technique of making the particle diameter of a catalyst to be filled in the reaction gas inlet side of a catalyst bed greater than that of a catalyst to be filled in the reaction gas outlet side of the catalyst bed.

When any of the catalyst filling methods described above is employed, productivity can be kept higher for a long term, while the hot spot temperature is controlled, even if load conditions, e.g., the concentration of acrolein in a reaction gas and the space velocity of the reaction gas, are set high.

The process of catalytic gas phase oxidation using a catalyst of the present invention will hereinafter be described; however, the process of catalytic gas phase oxidation is not limited to the following method, but can be applied to various known reaction methods such as a one-pass method and a recycle method, and may appropriately be altered or modified depending on the requirements.

In the present invention, acrolein and molecular oxygen may be supplied to a fixed-bed catalytic reactor filled with at least one catalyst containing the above specific amount of a volatile catalyst poison ingredient. If necessary, any of gases such as water vapor and an inert gas may be supplied to the catalytic reactor. For example, a mixed gas (if necessary, any other components than the following components may further be mixed therein) containing 1% to 15% by volume (preferably 4% to 12% by volume) of acrolein, 0.5% to 25% by volume (preferably 2% to 20% by volume) of molecular oxygen, 0% to 30% by volume (preferably 0% to 25% by volume) of water vapor, and 20% to 80% by volume (preferably 50% to 70% by volume) of at least one inert gas (e.g., nitrogen, carbon dioxide) may be supplied to the above catalytic reactor filled with the catalyst to bring the mixed gas into contact with the catalyst having the above features.

The ratio of oxygen/acrolein (by volume) in a reaction gas is preferably 0.7 to 2.0/1, more preferably 0.8 to 1.9/1, and still more preferably 0.9 to 1.8/1.

In this method, suitable reaction conditions may appropriately be set; for example, the reaction temperature may be 200° C. to 400° C. (preferably 220° C. to 380° C.) and the space velocity may be 300 to 10,000 $hr^{-1}$ STP (preferably 500 to 5,000 $hr^{-1}$ STP) under a pressure of 0.1 to 1 MPa. The reaction conditions may preferably be set so that the concentration of oxygen in an acrylic acid-containing gas flowing out of the catalytic reactor after the oxidation of acrolein becomes 0.5% to 8% by volume.

Of course, reaction gases contained in the mixed gas may be those which are obtained by various producing processes. For example, as acrolein, there can be used an acrolein-containing gas obtained in such a manner that propylene is subjected to catalytic gas phase oxidation with molecular oxygen in the presence of a catalyst containing molybdenum, bismuth, and iron. In this case, the acrolein-containing gas may be used as it is, or if necessary, at least one gas selected from the group consisting of air, oxygen, water vapor, inert gases, and other various gasses may be added thereto before or during use. The acrolein-containing gas may contain acetaldehyde and acetic acid as byproducts, and may further contain unreacted propane and propylene.

EXAMPLES

The present invention will hereinafter be further described by way of the following examples; however, it is not intended that the present invention is limited to these examples. In the examples, "part(s)" means "part(s) by mass".

Calculation of Supported Rate

Supported rate (% by mass)=[mass of catalyst component supported on a carrier (g)/(mass of catalyst component supported on a carrier (g)+mass of carrier (g))]×100

Acrolein Conversion

Acrolein conversion (mol %)=(mole number of reacted acrolein)/(mole number of supplied acrolein)×100

Propylene Conversion

Propylene conversion (mol %)=(mole number of reacted propylene)/(mole number of supplied propylene)×100

Preparation of Catalyst

Catalyst No. 1

While 25,000 parts of purified water was heated and stirred, 3,000 parts of ammonium molybdate, 861 parts of ammonium meta-vanadate, and 497 parts of ammonium para-tungustate were successively added and dissolved therein. Separately, while 2,000 parts of purified water was heated and stirred, 650 parts of copper nitrate trihydrate was added and dissolved therein. These two aqueous solutions were mixed with together, followed by addition of 41 parts of antimony trioxide and then 300 parts of 28% aqueous ammonium to obtain a suspension. The suspension was put in a porcelain evaporating dish on a hot water bath, and evaporated to dryness, while stirring with 2,500 parts of a spherical silica-alumina carrier having an average diameter of 5 mm, to allow the catalyst component to adhere to the carrier, followed by firing at 400° C. for 6 hours while flowing air, to obtain Catalyst No. 1. The supported rate of this catalyst was 25.1% by mass. The metal element composition, except oxygen atoms, of this catalyst is shown in Table 1.

Catalyst No. 2

Catalyst No. 2 was prepared in the same manner as described for Catalyst No. 1, except that 28% aqueous ammonium to be added was changed to 1,000 parts. The metal element composition of this catalyst, except oxygen atoms, is shown in Table 1.

Catalyst No. 3

Catalyst No. 3 was prepared in the same manner as described in Catalyst No. 1, except that 28% aqueous ammonium was not added. The metal element composition, except oxygen atoms, of this catalyst is shown in Table 1.

Catalyst No. 4

Catalyst No. 4 was prepared in the same manner as described for Catalyst No. 3 (without addition of 28% aqueous ammonium), except that the silica-alumina carrier having an average diameter of 5 mm to be put in the porcelain evaporating dish was changed to 3,000 parts. The metal element composition, except oxygen atoms, of this catalyst is shown in Table 1.

Catalyst No. 5

While 25,000 parts of purified water was heated and stirred, 3,000 parts of ammonium molybdate, 861 parts of ammonium meta-vanadate, and 497 parts of ammonium para-tungstate were added and dissolved therein. Separately, while 2,000 parts of purified water was heated and stirred, 650 parts of copper nitrate trihydrate and 43 parts of potassium nitrate were dissolved therein. These two aqueous solutions were mixed with together, followed by addition of 41 parts of antimony trioxide, to obtain a suspension. This suspension was put in a porcelain evaporating dish on a hot water bath, and evaporated to dryness, while stirring with 2,500 parts of a spherical silica-alumina carrier having an average diameter of 5 mm, to allow the catalyst component to adhere to the carrier, followed by firing at 400° C. for 6 hours while flowing air, to obtain Catalyst No. 5. The metal element composition, except oxygen atoms, of this catalyst is shown in Table 1.

Measurement of Content of Volatile Catalyst Poison Ingredient

First, 3 g of a catalyst component (in the case of a supported catalyst, a catalyst component removed from a carrier) is weighed precisely, and put into a clean glass vessel. The vessel is placed in a tubular furnace with a gas flowmeter (PROGRAMMABLE FURNANCE QF-02 manufactured by Mitsubishi Kasei K.K.). Then, three gas washing bottles (each of which has a volume of 25 cm$^3$ and has been allowed to contain 15 cm$^3$ of ion-exchanged water and then cooled to about 1° C. with ice water) are connected in series to the gas outlet side of the tubular furnace. While helium gas is allowed to pass at a rate of 100 cm$^3$/min through the tubular furnace, the catalyst component is heated at 500° C. for 60 minutes, and the total volume of a gas desorbed from the catalyst is introduced and collected into the gas washing bottles. After heating for 60 minutes, the temperature of the catalyst component is returned to room temperature, all the liquids in the gas washing bottles are put into a measuring flask, and ion-exchanged water is added to the measuring flask to the total liquid volume of 100 cm$^3$. The volatile catalyst poison ingredient in the catalyst component is measured with an ion chromatographic apparatus (type DX-320 manufactured by DIONEX; measuring conditions for ion chromatography are as follows: column, CS12A (for cations) ; oven and detector temperature, 35° C.; and sample solution injection rate, 5×10$^{-8}$m$^3$) using the liquid in the measuring flask as a sample solution, to calculate the content of the volatile catalyst poison ingredient per unit mass of the catalyst component.

The results of measurement of the volatile catalyst poison ingredients contained in Catalysts Nos. 1 to 5 (measured as an ammonium ion) are shown in Table 1.

TABLE 1

| Catalyst number | Catalyst composition | Supported rate (% by mass) | Content of volatile catalyst poison ingredient (ppb) |
|---|---|---|---|
| Catalyst No. 1 | $Mo_{12}V_{5.2}W_{1.3}Cu_{1.9}Sb_{0.2}$ | 25.1 | 18 |
| Catalyst No. 2 | $Mo_{12}V_{5.2}W_{1.3}Cu_{1.9}Sb_{0.2}$ | 25.1 | 52 |
| Catalyst No. 3 | $Mo_{12}V_{5.2}W_{1.3}Cu_{1.9}Sb_{0.2}$ | 25.0 | 8 |
| Catalyst No. 4 | $Mo_{12}V_{5.2}W_{1.3}Cu_{1.9}Sb_{0.2}$ | 19.8 | 7 |
| Catalyst No. 5 | $Mo_{12}V_{5.2}W_{1.3}Cu_{1.9}Sb_{0.2}K_{0.3}$ | 25.1 | 8 |

Acrolein Conversion

Reference Example 1

Catalyst No.1 obtained in Example 1 was filled in a stainless reaction tube having an inner diameter of 20 mm, which had been heated to 220° C. with a melted nitrate salt, so that a catalyst layer length became 200 mm, and the following reaction gas (A) was then introduced at a space velocity of 2,000 hr$^{-1}$ (STP) into the reaction tube for the catalytic gas phase oxidation of acrolein. The acrolein conversion after 24 hours from the reaction initiation is shown in Table 2.

Composition of Reaction Gas (A)

| Acrolein | 3.0% by volume |
|---|---|
| Oxygen | 6.0% by volume |
| Water vapor | 30.0% by volume |
| Inert gas such as nitrogen | 61.0% by volume |

Reference Examples 2 to 5

The catalytic gas phase oxidation of acrolein (Reference Example 2) was carried out in the same manner as described in Reference Example 1, except that Catalyst No. 2 was used in place of Catalyst No. 1. In addition, as Reference Examples 3, 4, and 5, the similar reaction was carried out using Catalysts Nos. 3, 4, and 5, respectively. The acrolein conversions after 24 hours from the reaction initiation are shown in Table 2.

TABLE 2

|  | Catalyst number | Acrolein conversion (% by mole) |
|---|---|---|
| Reference Example 1 | Catalyst No. 1 | 96.3 |
| Reference Example 2 | Catalyst No. 2 | 93.5 |
| Reference Example 3 | Catalyst No. 3 | 98.8 |
| Reference Example 4 | Catalyst No. 4 | 93.5 |
| Reference Example 5 | Catalyst No. 5 | 93.3 |

Example 1

Catalyst No. 1 was filled in a stainless reaction tube having an inner diameter of 25 mm, which had been heated with a melted nitrate salt, so that a catalyst layer length became 2,800 mm, and the following reaction gas (B) was then introduced at a space velocity of 1,600 hr$^{-1}$ (STP) into the reaction tube for the catalytic gas phase oxidation of acrolein. During this time, the reaction temperature was adjusted so that the acrolein conversion fell within the range of 98.7% to 99.3% by mole. The reaction temperature at the time of reaction initiation, the hot spot temperature after 24 hours from the reaction initiation, and the reaction temperature after 8,000 hours from the reaction initiation are shown in Table 3.

Composition of Reaction Gas (B):

| Acrolein | 4.0% by volume |
|---|---|
| Oxygen | 7.0% by volume |
| Water vapor | 25.0% by volume |
| Inert gas such as nitrogen | 64.0% by volume |

Comparative Example 1

The catalytic gas phase oxidation of acrolein was carried out in the same manner as described in Example 1, except that Catalyst No. 3 was filled in place of Catalyst No. 1. The reaction temperature at the time of reaction initiation, the hot spot temperature after 24 hours from the reaction initiation, and the reaction temperature after 8,000 hours from the reaction initiation are shown in Table 3.

Example 2

In a stainless reaction tube having an inner diameter of 25 mm, which had been heated with a melted nitrate salt, were filled Catalyst No. 2 (layer length: 800 mm) and Catalyst No. 3 (layer length: 2,000 mm) from the reaction gas inlet side towards the reaction gas outlet side. The following reaction gas (C) was then introduced at a space velocity of 1,800 hr$^{-1}$ (STP) into the reaction tube for the catalytic gas phase oxidation of acrolein. During this time, the reaction temperature was adjusted so that the acrolein conversion fell within the range of 98.7% to 99.3% by mole. The reaction temperature at the time of reaction initiation, the hot spot temperature after 24 hours from the reaction initiation, and the reaction temperature after 8,000 hours from the reaction initiation are shown in Table 3.

Composition of Reaction Gas (C)

| Acrolein | 6.0% by volume |
|---|---|
| Oxygen | 6.0% by volume |
| Water vapor | 25.0% by volume |
| Inert gas such as nitrogen | 63.0% by volume |

Comparative Example 2

The catalytic gas phase oxidation of acrolein was carried out in the same manner as described in Example 2, except that a catalyst dilution obtained by uniformly mixing silica-alumina balls having an average diameter of 5 mm and Catalyst No. 3 so that the volume ratio of the silica-alumina balls to Catalyst No. 3 became 1/4 was filled in place of Catalyst No. 2 (i.e., the dilution of Catalyst No. 3 was filled at a layer length of 800 mm in the catalyst bed on the reaction gas inlet side, and only Catalyst No. 3 was filled at a layer length of 2,000 mm in the catalyst bed on the reaction gas outlet side). The reaction temperature at the time of reaction initiation, the hot spot temperature after 24 hours from the reaction initiation, and the reaction temperature after 8,000 hours from the reaction initiation are shown in Table 3.

Comparative Examples 3, 4, and Example 3

The catalytic gas phase oxidation of acrolein was carried out in the same manner as described in Example 2, except that the catalyst filling method was changed as shown in Table 3. The results are shown in Table 3.

Examples 4 and 5

Preparation of Catalysts for Oxidation of Propylene

While 10,000 parts of purified water was heated with stirring, 1,500 parts of ammonium molybdate and 96 parts of ammonium para-tungstate were dissolved therein, and 425 parts of a 20% by mass silica sol was further added thereto. To this mixed solution was added dropwise, with stirring, a solution obtained by dissolving 1,236 parts of cobalt nitrate, 412 parts of nickel nitrate, 343 parts of iron nitrate, and 6.4 parts of potassium nitrate in 1,000 parts of purified water. Then, to this mixed solution was added dropwise, with stirring, a solution obtained by dissolving 446 parts of bismuth nitrate in an aqueous solution which had been obtained by adding 325 parts of concentrated nitric acid had to 500 parts of purified water. While the thus obtained suspension was heated with stirring, most of the water was evaporated to obtain a cake-like solid. This dried product was ground to obtain a powder, to which a 50% by mass aqueous ammonium nitrate solution was added as a binder, followed by kneading for 1 hour, and this kneaded material was formed by extrusion into a tubular shape (or a ring shape) having an outer diameter of 6.0 mm, a bore diameter of 2.0 mm, and a height of 6.6 mm. Then, this formed material was fired at 470° C. for 5 hours under an air stream to obtain Catalyst P1 for oxidation of propylene. The metal element composition, except oxygen atoms, of Catalyst P1 is as follows:

  Catalyst P1:

In addition, Catalyst P2 for oxidation of propylene was obtained in the same manner as described for the preparation of Catalyst P1, except that the catalyst size was changed to an outer diameter of 7.0 mm, a bore diameter of 3.0 mm, and a height of 7.7 mm.

Filling of Catalysts for Oxidizing Propylene

In a stainless reaction tube having an inner diameter of 25 mm, which had been heated with a melted nitrate salt, were filled Catalyst P2 (layer length: 1,000 mm) and Catalyst P1 (layer length: 2,000 mm) from the reaction gas inlet side towards the reaction gas outlet side.

Oxidation of Propylene

The reaction gas (D) (containing propylene (industrial propylene with a purity of 96%): 7% by volume, air: 60% by volume, water vapor: 8% by volume, and nitrogen: 24.7% by volume) was introduced at a space velocity of 1,600 hr$^{-1}$ (STP) into the above reaction tube filled with Catalysts P1 and P2 for the catalytic gas phase oxidation of propylene. During this time, the reaction temperature was adjusted so that the propylene conversion fell within the range of 95% to 96% by mole.

Oxidation of Acrolein

The gas obtained by oxidation of propylene was introduced into each of the reaction tubes filled with Catalysts Nos. 1, 2, and 3 in the combinations, orders, and layer lengths as shown in Table 3 for oxidation of acrolein, respectively. During this time, the reaction temperature was adjusted so that the acrolein conversion fell within the range of 98.7% to 99.3% by mole. The reaction temperature at the time of reaction initiation, the hot spot temperature after 24 hours from the reaction initiation, and the reaction temperature after 8,000 hours from the reaction initiation are shown in Table 3.

The above results with respect to the oxidation of acrolein were calculated on the assumption that gasses other than acrolein, such as propylene, propane, acrylic acid, and acetic acid, in the mixed gas introduced into the reaction tube did not cause any reaction.

TABLE 3

| | Catalyst filling method (gas inlet side → gas outlet side) | Reaction temperature at the time of reaction initiation (° C.) | Hot spot temperature after 24 hours from the reaction initiation (° C.) | Reaction temperature after 8,000 hours from the reaction initiation (° C.) |
|---|---|---|---|---|
| Example 1 | Catalyst No. 1 (2,800 mm) | 255 | 317 | 259 |
| Comparative Example 1 | Catalyst No. 3 (2,800 mm) | 252 | 319 | 262 |
| Example 2 | Catalyst No. 2 (800 mm) → Catalyst No. 3 (2,000 mm) | 260 | 335 | 266 |
| Comparative Example 2 | Catalyst No. 3 dilution (800 mm) → Catalyst No. 3 (2,000 mm) | 260 | 340 | 276 |
| Comparative Example 3 | Catalyst No. 4 (800 mm) → Catalyst No. 3 (2,000 mm) | 260 | 340 | 277 |
| Comparative Example 4 | Catalyst No. 5 (800 mm) → Catalyst No. 3 (2,000 mm) | 260 | 339 | 274 |
| Example 3 | Catalyst No. 2 (800 mm) → Catalyst No. 1 (2,000 mm) | 263 | 340 | 270 |
| Example 4 | Catalyst No. 2 (600 mm) → Catalyst No. 1 (600 mm) → Catalyst No. 3 (1,600 mm) | 264 | 341 | 278 |
| Example 5 | Catalyst No. 1 (200 mm) → Catalyst No. 2 (700 mm) → Catalyst No. 3 (1,900 mm) | 262 | 342 | 278 |

The invention claimed is:

1. A catalyst for catalytic gas phase oxidation of acrolein with molecular oxygen to produce acrylic acid, the catalyst comprising molybdenum and vanadium and further comprising a volatile catalyst poison ingredient in an amount of 10 to 100 ppb by mass as measured by ion chromatography.

2. The catalyst according to claim 1, wherein the volatile catalyst poison ingredient is detected as an inorganic ion by ion chromatography.

3. The catalyst according to claim 2, wherein the inorganic ion is an ammonium ion.

4. A process for producing acrylic acid, comprising a step of carrying out catalytic gas phase oxidation of acrolein with molecular oxygen using a catalyst, wherein the catalyst comprises molybdenum and vanadium and further comprises a volatile catalyst poison ingredient in an amount of 10 to 100 ppb by mass as measured by ion chromatography.

5. The process for producing acrylic acid according to claim 4, wherein the catalytic gas phase oxidation of acrolein with molecular oxygen is carried out with a fixed-bed shell-and-tube catalytic reactor with a catalyst bed containing the catalyst.

6. The process for producing acrylic acid according to claim 5, wherein a content of the volatile catalyst poison ingredient in the catalyst is set substantially constant over the catalyst bed.

7. The process for producing acrylic acid according to claim 5, wherein the catalyst bed is divided into two or more parts in a tube axial direction of the catalytic reactor and wherein a content of the volatile catalyst poison ingredient in the catalyst is set lower in one part of the catalyst bed positioned on a reaction gas outlet side of the catalyst bed than in another part, adjacent to said one part, of the catalyst bed positioned on a reaction gas inlet side of the catalyst bed.

8. The process for producing acrylic acid according to claim 5, wherein the catalyst bed is divided into three or more parts in a tube axial direction of the catalytic reactor and wherein a content of the volatile catalyst poison ingredient in the catalyst is set lower in one part of the catalyst bed positioned on a reaction gas outlet side of the catalyst bed than in another part of the catalyst bed positioned on a reaction gas inlet side of the catalyst bed and wherein the content of the volatile catalyst poison ingredient in the catalyst shows a rise and then lowering in an intermediate part of the catalyst bed positioned between the reaction gas inlet side and the reaction gas outlet side of the catalyst bed.

9. The process for producing acrylic acid according to claim 4, wherein the acrolein is obtained by preceding oxidation in which propylene is subjected to catalytic gas phase oxidation with molecular oxygen in the presence of a catalyst comprising molybdenum, bismuth, and iron.

10. The process according to claim 4, wherein the volatile catalyst poison ingredient is detected as an inorganic ion by ion chromatography.

11. The process according to claim 10, wherein the inorganic ion is an ammonium ion.

* * * * *